United States Patent
Li et al.

(10) Patent No.: US 9,669,221 B2
(45) Date of Patent: *Jun. 6, 2017

(54) SYSTEM TO DETECT LEAD LOCATION FROM MEDICAL IMAGE

(71) Applicant: Boston Scientific Neuromodulation Corporation, Valencia, CA (US)

(72) Inventors: Yue Li, Sherman Oaks, CA (US); Dennis Zottola, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/147,304

(22) Filed: May 5, 2016

(65) Prior Publication Data

US 2016/0243367 A1    Aug. 25, 2016

Related U.S. Application Data

(63) Continuation of application No. 14/528,461, filed on Oct. 30, 2014, now Pat. No. 9,333,361.

(Continued)

(51) Int. Cl.
*A61N 1/00* (2006.01)
*A61N 1/36* (2006.01)
(Continued)

(52) U.S. Cl.
CPC ............ *A61N 1/36182* (2013.01); *A61B 6/12* (2013.01); *A61N 1/36071* (2013.01);
(Continued)

(58) Field of Classification Search
CPC .............. A61N 1/37264; A61N 1/0551; A61N 1/36185; A61N 1/37247; G06T 7/0042; G06T 7/0012
See application file for complete search history.

(56) References Cited

U.S. PATENT DOCUMENTS

| 5,938,690 A | 8/1999 | Law et al. |
| 5,941,906 A | 8/1999 | Barreras, Sr. et al. |

(Continued)

FOREIGN PATENT DOCUMENTS

| WO | WO-2006029257 A2 | 3/2006 |
| WO | WO-2006135791 A2 | 12/2006 |

(Continued)

OTHER PUBLICATIONS

"U.S. Appl. No. 14/528,461, Notice of Allowance mailed Jan. 14, 2016", 8 pgs.

(Continued)

*Primary Examiner* — Robert N Wieland
(74) *Attorney, Agent, or Firm* — Schwegman Lundberg & Woessner, P.A.

(57) ABSTRACT

An external control system for use with a neurostimulation device and at least one neurostimulation lead implanted within the tissue of a patient is provided. The external control system comprises a user interface configured for receiving input from a user, output circuitry configured for communicating with the neurostimulation device, and control/processing circuitry configured for receiving a medical image of the neurostimulation lead(s) relative to an anatomical structure, processing the medical image to detect the location of the neurostimulation lead(s) relative to the anatomical structure, generating a set of stimulation parameters based on the user input and the detected location of the neurostimulation lead(s) relative to the anatomical structure, and directing the output circuitry to transmit instructions to the neurostimulation device to convey electrical stimulation energy in accordance with the stimulation parameter set.

20 Claims, 9 Drawing Sheets

Related U.S. Application Data

(60) Provisional application No. 61/898,401, filed on Oct. 31, 2013.

(51) Int. Cl.
*A61N 1/372* (2006.01)
*A61B 6/12* (2006.01)
*A61B 6/00* (2006.01)

(52) U.S. Cl.
CPC ..... *A61N 1/36185* (2013.01); *A61N 1/37247* (2013.01); *A61B 6/506* (2013.01)

(56) References Cited

U.S. PATENT DOCUMENTS

| | | | |
|---|---|---|---|
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,979,133 B2 | 7/2011 | Feler et al. | |
| 7,987,000 B2 | 7/2011 | Moffitt et al. | |
| 8,019,439 B2 | 9/2011 | Kuzma et al. | |
| 8,160,328 B2 | 4/2012 | Goetz et al. | |
| 8,180,129 B2 | 5/2012 | Goetz et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,412,345 B2 | 4/2013 | Moffitt | |
| 8,437,857 B2 | 5/2013 | Moffitt et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 | 2/2014 | Alataris et al. | |
| 8,660,653 B2 | 2/2014 | Kothandaraman | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,700,178 B2 | 4/2014 | Anderson | |
| 8,731,675 B2 | 5/2014 | Ranu et al. | |
| 8,751,009 B2 | 6/2014 | Wacnik | |
| 8,788,054 B2 | 7/2014 | Kothandaraman et al. | |
| 8,909,350 B2 | 12/2014 | Lee | |
| 9,333,361 B2 | 5/2016 | Li et al. | |
| 2003/0139781 A1 | 7/2003 | Bradley et al. | |
| 2004/0116978 A1 | 6/2004 | Bradley | |
| 2007/0021801 A1 | 1/2007 | Heruth et al. | |
| 2007/0150036 A1 | 6/2007 | Anderson | |
| 2007/0203538 A1* | 8/2007 | Stone | A61N 1/37247 607/59 |
| 2008/0188909 A1 | 8/2008 | Bradley | |
| 2009/0196472 A1 | 8/2009 | Goetz et al. | |
| 2009/0198306 A1 | 8/2009 | Goetz et al. | |
| 2009/0204173 A1 | 8/2009 | Fang et al. | |
| 2010/0010566 A1 | 1/2010 | Thacker et al. | |
| 2010/0121409 A1 | 5/2010 | Kothandaraman et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0093047 A1 | 4/2011 | Davis et al. | |
| 2011/0282414 A1 | 11/2011 | Kothandaraman et al. | |
| 2012/0059446 A1 | 3/2012 | Wallace et al. | |
| 2012/0083709 A1 | 4/2012 | Parker et al. | |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2013/0066411 A1 | 3/2013 | Thacker et al. | |
| 2013/0116752 A1 | 5/2013 | Parker et al. | |
| 2013/0131760 A1 | 5/2013 | Rao et al. | |
| 2013/0158628 A1 | 6/2013 | Kothandaraman | |
| 2013/0268021 A1 | 10/2013 | Moffitt | |
| 2013/0296975 A1 | 11/2013 | Lee et al. | |
| 2014/0081349 A1 | 3/2014 | Lee et al. | |
| 2014/0277267 A1 | 9/2014 | Vansickle et al. | |
| 2014/0371819 A1 | 12/2014 | Goetz et al. | |
| 2015/0119958 A1 | 4/2015 | Li et al. | |

FOREIGN PATENT DOCUMENTS

| | | |
|---|---|---|
| WO | WO-2009097224 A1 | 8/2009 |
| WO | WO-2015066295 A1 | 5/2015 |

OTHER PUBLICATIONS

"U.S. Appl. No. 14/528,461, Response filed Dec. 3, 2015 to Non Final Office Action mailed Sep. 8, 2015", 11 pgs.

"U.S. Appl. No. 14/528,461, Non Final Office Action mailed Sep. 8, 2015", 14 pgs.

"International Application Serial No. PCT/US2014/63103, International Search Report mailed Jan. 8, 2015", 4 pgs.

"International Application Serial No. PCT/US2014/63103, Written Opinion mailed Jan. 8, 2015", 4 pgs.

* cited by examiner

SYSTEM TO DETECT LEAD LOCATION FROM MEDICAL IMAGE

CLAIM OF PRIORITY

This application is a continuation of U.S. application Ser. No. 14/528,461, filed Oct. 30, 2014, now issued as U.S. Pat. No. 9,333,361, which claims the benefit of priority under 35. U.S.C. §119(e) of U.S. Provisional Patent Application Ser. No. 61/898,401, filed on Oct. 31, 2013, each of which is herein incorporated by reference in its entirety.

FIELD OF THE INVENTION

The present invention relates to medical systems, and more particularly, to a user interface for programming neuromodulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

In the context of an SCS procedure, one or more neurostimulation leads are introduced through the patient's back into the epidural space, such that the electrodes carried by the leads are arranged in a desired pattern and spacing to create an electrode array. Multi-lead configurations have been increasingly used in electrical stimulation applications. In the neurostimulation application of SCS, the use of multiple leads increases the stimulation area and penetration depth (therefore coverage), as well as enables more combinations of anodic and cathodic electrodes for stimulation, such as transverse multipolar (bipolar, tripolar, or quadrapolar) stimulation, in addition to any longitudinal single lead configuration. After proper placement of the neurostimulation leads at the target area of the spinal cord, the leads are anchored in place at an exit site to prevent movement of the neurostimulation leads.

To facilitate the location of the neurostimulator away from the exit point of the neurostimulation leads, lead extensions are sometimes used. The neurostimulation leads, or the lead extensions, are then connected to the IPG, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead(s) being placed in a location (both longitudinal and lateral) relative to the spinal tissue, such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

As such, the CP (described briefly above) may be used to instruct the neurostimulator to apply electrical stimulation to test placement of the leads and/or electrodes inter-operatively (i.e., in the context of an operating room (OR) mapping procedure), thereby assuring that the leads and/or electrodes are implanted in effective locations within the patient. The patient may provide verbal feedback regarding the presence of paresthesia over the pain area, and based on this feedback, the lead positions may be adjusted and re-anchored if necessary. Any incisions are then closed to fully implant the system.

Post-operatively (i.e., after the surgical procedure has been completed), a fitting procedure, which may be referred to as a navigation session, may be performed using the CP to program the RC, and if applicable the IPG, with a set of stimulation parameters that best addresses the painful site, thereby optimizing or re-optimizing the therapy. Thus, the navigation session may be used to pinpoint the stimulation region or areas correlating to the pain. Such programming ability is particularly advantageous after implantation should the leads gradually or unexpectedly move, which if uncorrected, would relocate the paresthesia away from the pain site.

Whether used inter-operatively or post-operatively, a computer program, such as Bionic Navigator®, available from Boston Scientific Neuromodulation Corporation, can be incorporated in the CP to provide a computer-guide programming system that facilitates selection of the stimulation parameters. The Bionic Navigator® is a software package that operates on a suitable computer and allows clinicians to program stimulation parameters into an external handheld programmer (referred to as a remote control). Each set of stimulation parameters, including fractionalized current distribution to the electrodes (as percentage cathodic current, percentage anodic current, or off), programmed by the Bionic Navigator® may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes based on a representation of the physical electrode arrangement displayed on the computer screen of the CP, or may be operated by the clinician in a "semi-automatic mode" to electrically "steer" the current along the implanted leads in real-time, thereby allowing the clinician to determine the most efficacious stimulation parameter sets that can then be stored and eventually combined into stimulation programs. In the navigation mode, the Bionic Navigator® can store selected fractionalized electrode configurations that can be displayed to the clinician as marks representing corresponding stimulation regions relative to the electrode array.

It may sometimes be desirable to estimate or predict the stimulation effects of electrical energy applied, or to be applied, to neural tissue adjacent to electrodes based on an estimation of the membrane response (e.g. transmembrane voltage potentials) of one or more neurons induced by the actually applied or potentially applied electrical energy. For example, given a specific set of stimulation parameters, it may be desired to predict a region of stimulation within the neural tissue of a patient based on an estimation of the neuronal response. As another example, when transitioning between electrode configurations, it may be desirable to adjust the intensity of the electrical stimulation energy based on an estimation of the transmembrane voltage potentials. Such a stimulation prediction software program can be incorporated into a CP to provide it with the capability of predicting a tissue region of stimulation to facilitate the determination of an optimum set of stimulation parameter and for actually stimulating the tissue region in accordance with the optimum stimulation parameter set.

Implantable lead positioning information is critical in SCS for both computer-guided programming systems and simulation/modeling systems.

For example, with respect to side-by-side electrode configurations, it is important that the CP, whether operated in a "manual mode" or "semi-automatic mode," have knowledge of the lead stagger (i.e., the degree to which the first electrode of one lead is vertically offset from the first electrode of another lead) (or even lateral offset and/or angle of each lead relative to the midline of the spinal cord) either because the physician initially implanted the electrode leads in this manner to maximize the therapeutic effect of the stimulation or because the electrode leads subsequently migrated from an initially unstaggered configuration.

For example, if a representation of the relative positions of the leads is incorrectly displayed to the user during operation of the CP in the manual mode, it is possible that the electrode configurations selected by the user will be ineffective. Similarly, because the algorithm used to operate the CP in the semi-automatic mode relies heavily on the extent to which the leads are staggered, if the relative positions of the leads are improperly input into the CP, the current steering resulting from the semi-automatic mode may be ineffective.

Furthermore, it is also important that the CP have knowledge of the longitudinal position of the neurostimulation lead or leads relative to the vertebral segments, since it is known that the thickness of the cerebral spinal fluid (CSF) varies along the length of the spinal cord, with the thickness of the CSF increasing in the caudal direction. The neurostimulation lead(s) may be subjected to a different volume of CSF depending on their location relative to the longitudinal vertebral segments. As the CSF become thicker, it becomes more difficult to stimulate the spinal cord tissue without causing side-effects. As such, different electrode combinations may be appropriate for different lead implantation locations along the spinal cord.

The conventional manner in which lead positioning information is obtained is through fluoroscopy or static X-ray images, and in particular, reading the fluoroscopic or static X-ray images, identifying the location of the lead(s) relative to the segmental level, manually entering the data into the CP, and visualizing it with a predefined homogenous user interface (UI) model. In one example, with knowledge of the lead positioning information obtained from a medical image, such as an X-ray image, graphical leads representing the actual leads implanted within the patient are dragged and dropped on top of a homogenous spinal column model graphically displayed on the user interface, as described in U.S. patent application Ser. No. 13/104,826, entitled "System and Method for Defining Neurostimulation Lead Configuration," which is expressly incorporated herein by reference.

Normally, the fluoroscopic or static X-ray images are translated into a very rough approximation of the actual location of the implanted neurostimulation lead(s) relative to the longitudinal vertebral segments (e.g., "around T7" or "between T7 and T8"). Furthermore, the manual process of inputting the lead position data into the CP could sometimes introduce errors; for example, the user may input incorrect lead position information (offsets, angles, etc.) by mistake, or precision error due to screen resolution as well as human eyes may limit the accuracy of the lead position information if using a drag-and-drop procedure. Inaccurate lead positioning could affect the output result of the computer-guided electrode programming algorithms that assume accurate electrode positions, resulting in a less therapeutic benefit. Furthermore, because the CP utilizes a homogenous anatomical model generated across a population that assumes that all patients have almost identical size of the spinal cord, computer-guided programming algorithms sometimes do not generate effective protocols due to the variation between individual patients.

Detecting lead positioning information directly from fluoroscopic or static X-ray images could provide more accurate information about an individual patient while also largely avoiding human-introduced errors. However, all currently available lead position detection techniques have limitations when used with computer-guided electrode programming algorithms in the context of post-op programming of the leads. In particular, those methods can only process post-operation imaging data, since it involves additional efforts, e.g., exporting image data, copying image data onto a USB drive, importing into commercial software on a separate computer, processing the images, identifying lead location, and then switching to a CP to manually enter lead information, which takes a relatively long time making it impossible to complete the whole process during or shortly after surgery.

There, thus, remains a need for a system or method that enables detecting and locating neurostimulation lead(s) relative to an anatomical structure, such as the spinal column, using medical images, such as fluoroscopic or static X-ray images, which would provide the possibility for real-time programming or simulation both in an intra-op and post-op environment.

SUMMARY OF THE INVENTION

In accordance with the present inventions, an external control system for use with a neurostimulation device and at least one neurostimulation lead implanted within the tissue of a patient is provided. The external control system comprises a user interface configured for receiving input from a user, and output circuitry (e.g., telemetry circuitry) configured for communicating with the neurostimulation device. The external control system further comprises control/processing circuitry configured for receiving a medical image (e.g., a fluoroscopic image or a static X-ray image) of the neurostimulation lead(s) relative to an anatomical structure, processing the medical image (e.g., using an image segmentation and/or pattern recognition technique) to detect the location of the neurostimulation lead(s) relative to the anatomical structure, generating a set of stimulation parameters based on the user input and the detected location of the neurostimulation lead(s) relative to the anatomical structure, and directing the output circuitry to transmit instructions to the neurostimulation device to convey electrical stimulation energy in accordance with the stimulation parameter set.

In one embodiment, the anatomical structure is a spinal column, in which case the detected location may be the longitudinal location of the neurostimulation lead(s) relative to the spinal column. The longitudinal location of the neurostimulation lead(s) may be a linear interpolation between two adjacent vertebral segments of the spinal column, in which case, the control/processing circuitry may be configured for locating the graphical representation of the neurostimulation lead(s) relative to two corresponding adjacent vertebral segments. The control/processing circuitry may optionally be configured for processing the medical image to detect the angle of the neurostimulation lead(s) relative to the midline of the spinal column, and for generating the stimulation parameter set further based on the detected angle of the neurostimulation lead(s) relative to the spinal column. If multiple neurostimulation leads are provided, the control/processing circuitry may be configured for processing the medical image to detect the locations of the neurostimulation leads relative to each other, and for generating the stimulation parameter set further based on the detected relative locations of the neurostimulation leads.

In one embodiment, the control/processing circuitry is further configured for displaying a graphical representation of the neurostimulation lead(s) relative to a representation of the anatomical structure (e.g., a graphical model of the anatomical structure or even the medical image of the anatomical structure, itself). The user interface may include a directional control device for receiving the user input, in which case, the control/processing circuitry may be configured for generating a plurality of stimulation parameters that define different electrode combinations based on the user input into the directional control device and the detected location of the neurostimulation lead(s) relative to the anatomical structure, and directing the output circuitry to transmit instructions to the neurostimulation device to deliver electrical stimulation energy in accordance with the stimulation parameter sets.

In an optional embodiment, the user interface is configured for displaying the medical image, and allowing the user to define an anatomical landmark on the anatomical structure, in which case, the control/processing circuitry may be configured for detecting the location of the neurostimulation lead(s) relative to the anatomical landmark, and for generating the stimulation parameter set based on the detected location of the neurostimulation lead(s) relative to the anatomical landmark.

In another optional embodiment, the neurostimulation lead(s) carries a plurality of electrodes, and the control/processing circuitry is configured for determining the locations of the electrodes relative to each other, and for generating the stimulation parameter set further based on the determined electrode locations. For example, the external control system may comprise a memory configured for storing a look-up table of different types of neurostimulation leads and corresponding electrode spacings, electrode size, layout pattern, etc. for the different types of neurostimulation leads, in which case, the control/processing circuitry may be configured for processing the medical image to identify the type of the neurostimulation lead(s), acquiring the electrode spacings, electrode size, layout pattern, etc. corresponding to the identified type in the look-up table, and determining the locations of the electrodes based on the acquired electrode spacings, electrode size, layout pattern, etc.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of brain tissue.

Figure 1:
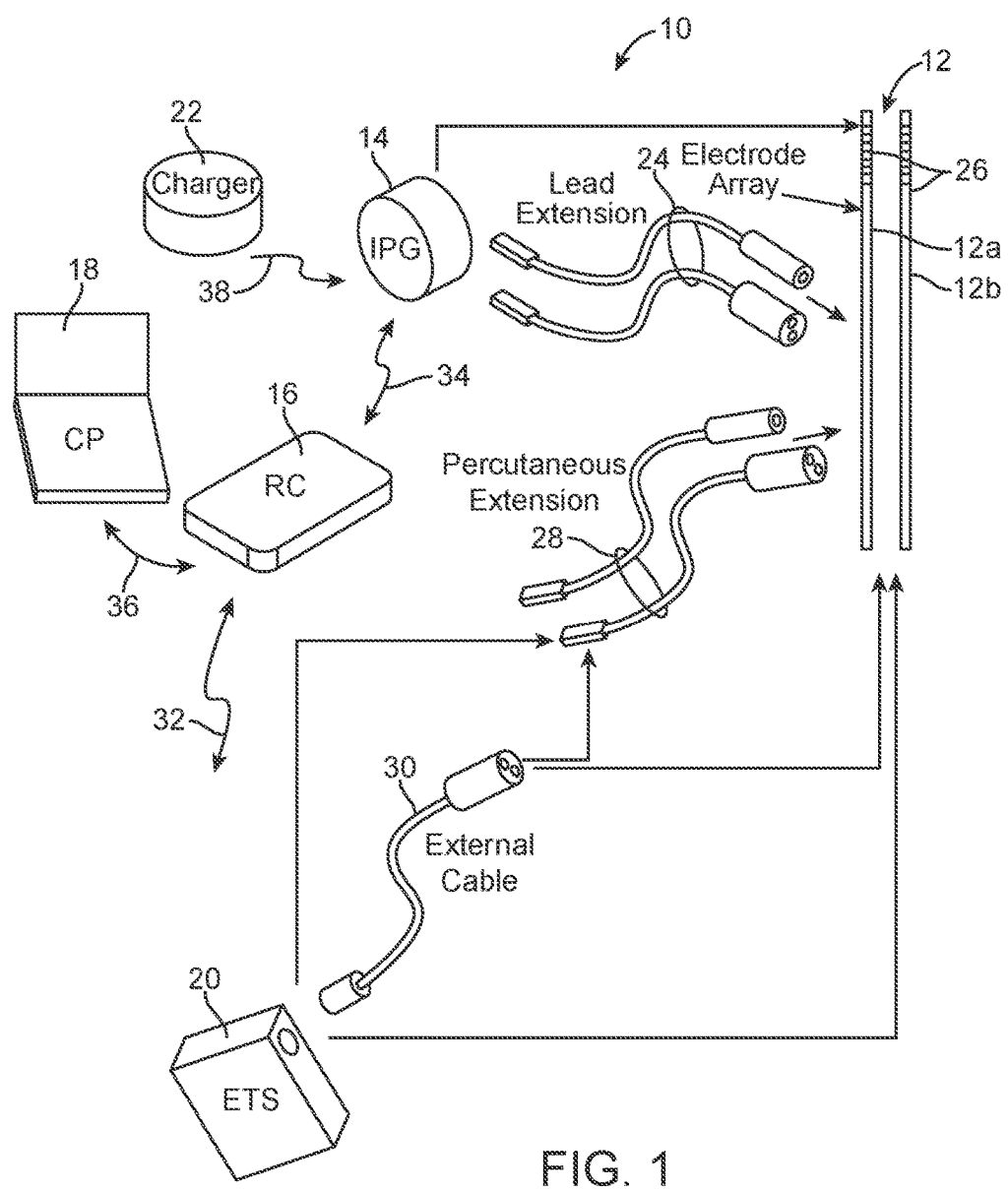
FIG. 1 is perspective view of one embodiment of a SCS system arranged in accordance with the present inventions.

Turning first to FIG. 1, an exemplary SCS system 10 generally includes a plurality (in this case, two) of implantable neurostimulation leads 12, an implantable pulse generator (IPG) 14, an external remote controller (RC) 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. As will be described in further detail below, the electrodes 26 may alternatively be arranged in a two-dimensional pattern on a single paddle lead.

The IPG 14 includes pulse generation circuitry that delivers electrical stimulation energy in the form of a pulsed electrical waveform (i.e., a temporal series of electrical pulses) to the electrode array 26 in accordance with a set of stimulation parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the IPG 14, RC 16, ETS 20, and external charger 22 will not be described herein. Details of exemplary embodiments of these devices are disclosed in U.S. Pat. No. 6,895,280, which is expressly incorporated herein by reference.

Figure 2:
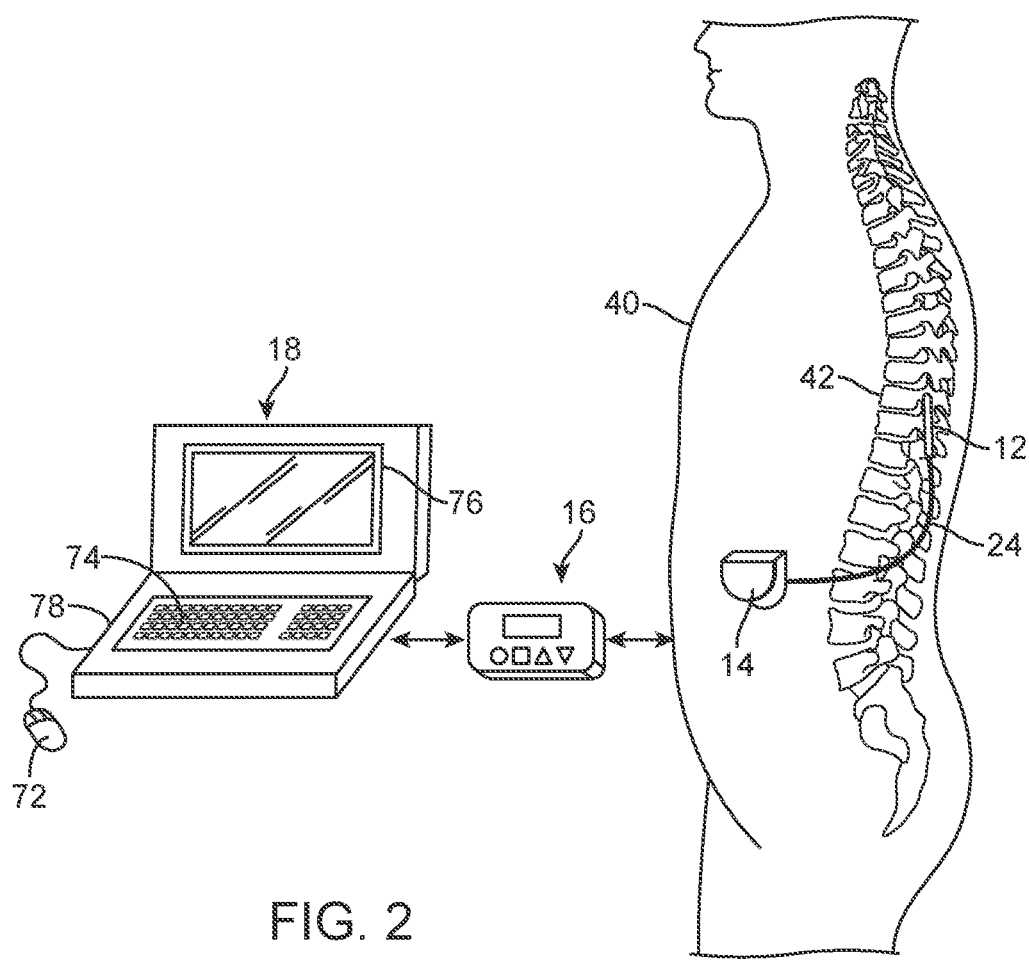
FIG. 2 is a plan view of the SCS system of FIG. 1 in use with a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension(s) 24 facilitate locating the IPG 14 away from the exit point of the neurostimulation leads 12. As there shown, the CP 18 communicates with the IPG 14 via the RC 16.

Figure 3:
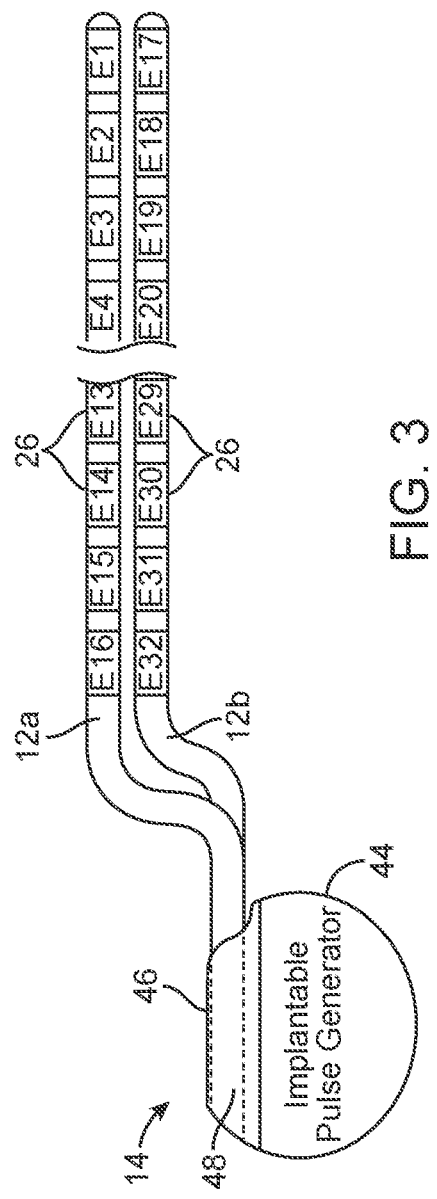
FIG. 3 is a side view of an implantable pulse generator and a pair of percutaneous neurostimulation leads that can be used in the SCS system of FIG. 1.

Referring to FIG. 3, the IPG 14 further comprises an outer case 44 for housing the electronic and other components (described in further detail below), and a connector 46 to which the proximal end of the neuromodulation leads 12 mate in a manner that electrically couples the electrodes 26 to the internal electronics (including the battery and the pulse generation circuitry) within the outer case 44. To this end, the connector 46 includes one or more ports 48 for receiving the proximal end(s) of the neurostimulation lead(s). In the case where the lead extension(s) 24 are used, the port(s) 48 may instead receive the proximal end(s) of such lead extension(s) 24. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

In the embodiment illustrated in FIG. 3, the neurostimulation leads 12 take the form of percutaneous leads on which the electrodes 26 (in this case, electrodes E1-E32) are disposed as ring electrodes. In the illustrated embodiment, two percutaneous leads 12a and 12b on which electrodes E1-E16 and E17-E32 are respectively disposed can be used with the SCM system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
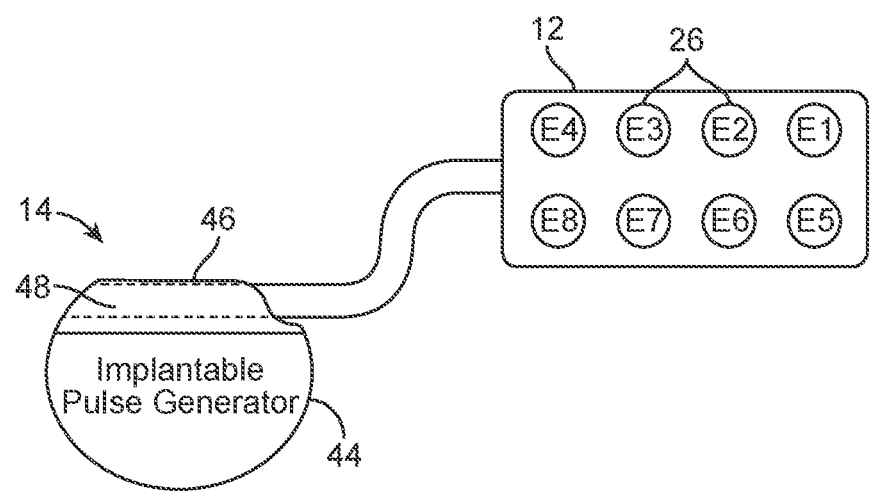
FIG. 4 is a side view of an implantable pulse generator and a surgical paddle neurostimulation lead that can be used in the SCS system of FIG. 1.

In an alternative embodiment illustrated in FIG. 4, the neurostimulation lead 12 takes the form of a surgical paddle lead 12 on which the electrodes 26 (in this case, electrodes E1-E8) are carried. The electrodes 26 are arranged in a two-dimensional array in two columns along the axis of the neurostimulation lead 12. In the illustrated embodiment, the electrodes 26 are arranged in two columns of electrodes 26 (electrodes E1-E4 in the first column, and electrodes E5-E8 in the second column). The actual number of leads and electrodes will, of course, vary according to the intended application. The surgical paddle design facilitates placement of the modulating electrodes in regions intra-spinally, intracranially, or subcutaneously where separation between the electrodes and the nerves of interest is minimized (e.g., minimal cerebral spinal fluid thickness, epidural, and close to nerve roots (i.e., "in the gutter"). Preferably, the electrodes have a large surface area to reduce the impedance and thus, the necessarily energy consumption. Further details regarding the construction and method of manufacture of surgical paddle leads are disclosed in U.S. patent application Ser. No. 11/319,291, entitled "Stimulator Leads and Methods for Lead Fabrication," and U.S. patent application Ser. No. 12/204,094, entitled "Multiple Tunable Central Cathodes on a Paddle for Increased Medial-Lateral and Rostro-Caudal Flexibility via Current Steering," the disclosures of which are expressly incorporated herein by reference.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc, can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry (not shown) that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 5:
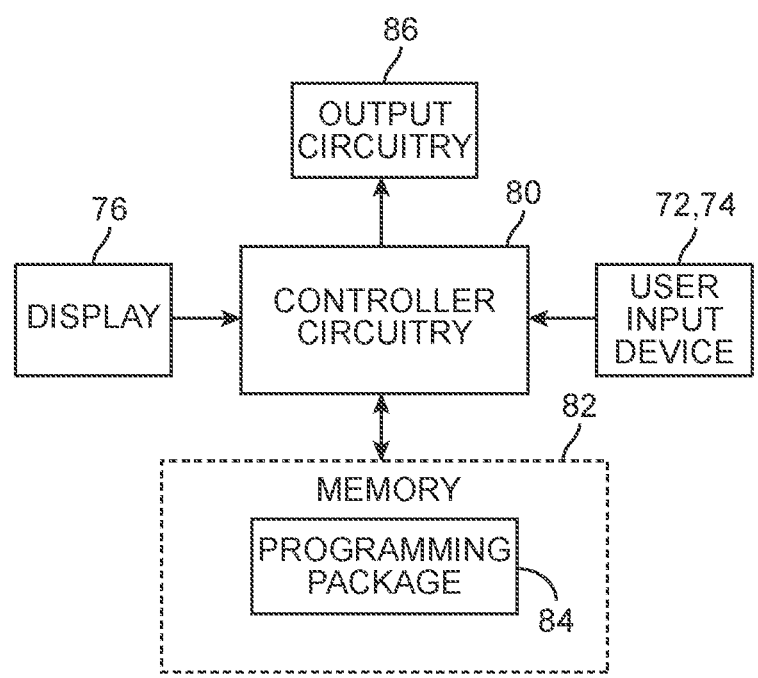
FIG. 5 is a block diagram of the components of a clinician programmer that can be used in the SCS system of FIG. 1.

As shown in FIG. 5, the CP 18 generally includes control/processing circuitry 80 (e.g., a central processor unit (CPU)) and memory 82 that stores a stimulation programming package 84, which can be executed by the control/processing circuitry 80 to allow the user to program the IPG 14, and RC 16. The CP 18 further includes input/output circuitry 86 for downloading stimulation parameters to the IPG 14 and RC 16 and for uploading stimulation parameters already stored in the memory 66 of the IPG 14 or RC 16, as well as for acquiring medical image data from an external device, as will be described in further detail below.

Execution of the programming package 84 by the control/processing circuitry 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, the CP 18 is capable of automatically receiving from an external source a medical image (such as a fluoroscopic image or a static X-ray image) of the neurostimulation leads 12 and the spinal column 42 of the patient 40 (in this case, the segmental level of the neurostimulation leads 12), and processing the medical image to detect the location of the neurostimulation leads 12 relative to the spinal column 42. The CP 18 may also detect the locations of the neurostimulation leads 12 relative to each other, as well as detecting the angle of the neurostimulation leads 12 relative to a midline of the spinal column 42, and detecting the type of neurostimulation leads 12. As will be discussed in further detail below, the CP 18 utilizes this detected lead information to generate the proper set of stimulation parameters in accordance with which the electrical stimulation energy will be subsequently delivered, as well as displaying graphical representations of the neurostimulation leads 12 relative to a representation of the spinal column 42.

To this end, one technique for acquiring and processing a medical image will now be described with reference to FIG. 6. First, one or more neurostimulation leads 12 (in this case, the two neurostimulation leads 12 illustrated in FIG. 3) are implanted within the spinal column 42 of the patient 40 under guidance of fluoroscopy using a conventional fluoroscopy machine 90. Once the neurostimulation leads 12 are properly located, as confirmed by feedback from the patient in response to delivery of electrical stimulation energy, and affixed within the spinal column 42, a medical image 92, such as a fluoroscopic image or a static X-ray image, is acquired using the fluoroscopy machine 90. As shown, medical image 92 is of the electrodes 26 carried by the neurostimulation leads 12 and the spinal column 42. That is, as is typical with fluoroscopic or static X-ray images, relatively dense material, such as metal and bone (in this case, the electrodes 26 and the vertebrae of the spinal column 42), will appear in the medical image 92, while the less dense material will be transparent.

The medical image 92, in the form of conventional DICOM image data, can then be transmitted from the fluoroscopy machine 90 to the CP 18. The technique used to transfer the DICOM image data will be based on the type of the fluoroscopy machine 90. For example, if the fluoroscopy machine 90 supports networking, the DICOM image data can be directly acquired via wired cable 94 or wireless though a local area network (LAN) 96. If the fluoroscopy machine 90 supports only USB output, a wireless USB data transmitting device 98 can be used to relay the DICOM image data to the CP 18. If the fluoroscopy machine 90 does not have either of these features, a low-cost high-resolution video camera 99 can be used to capture the images displayed on the fluoroscopy machine 90, which recorded images can then be transferred to the CP 18 through a LAN in video/image streams. However the medical image data is transferred, the input/output circuitry 86 of the CP 18 will be adapted to receive the DICOM image data or video/image stream data from the fluoroscopy machine 90 either through the wired cable 94 or wirelessly through the LAN 96. Once the CP 18 receives the medical image data from the fluoroscopy machine 90, it processes the image data using conventional image segmentation and pattern recognition techniques.

In particular, the CP 18 can process the image data to determine the location of the neurostimulation leads 12 relative to the main vertebral segments (e.g., at T7 or T8). More accurate positional information may be computed using linear interpolation between the vertebral segments (e.g., one-quarter of the distance between from the center of T7 to the center of T8). The location of the neurostimulation leads 12 may be identified by reference points on the neurostimulation leads 12 (e.g., the distal tip of the neurostimulation leads 12 or the centers of the distal-most electrodes 26). The CP 18 is also capable of identifying the locations of the neurostimulation leads 12 relative to each other (e.g., the locations of the distal tips of the neurostimulation leads 12 relative to each other or the locations of the centers of the distal-most electrodes 26 relative to each other).

Although the distal tips of the neurostimulation leads 12 are not identifiable in the medical image data, the CP 18 is capable of determining the locations of the distal tips based on identified locations of the electrodes 26 (e.g., the distal-most electrodes 26) using a known distance between the distal tip of the neurostimulation lead 12 and the distal-most electrode 26 (i.e., the known distance is added onto the identified location of the distal-most electrode 26 to obtain the location of the distal tip of the neurostimulation lead 12). The known distance between the distal tip of the neurostimulation lead 12 and the distal-most electrode 26 can be obtained, e.g., from a look-up table stored in the memory 66. The look-up table comprises a list of known distances for corresponding neurostimulation lead types. The type of the neurostimulation leads 12 may either be manually input into the CP 18 or can be automatically detected by the CP 18 by recognizing layout patterns of the electrodes 26 in the medical image data. In an alternative embodiment, the CP 18 only identifies one electrode 26 for each of the neurostimulation leads 12 from the medical image data, and then determines the locations of the remaining electrodes 26 based on known electrode spacings correlated to the type of neurostimulation leads 12 obtained from the look-up table.

As briefly discussed above, the CP 18 can process the image data to determine the tilt angle of the neurostimulation leads 12 relative to the midline of the spinal column 42. In particular, if the midline of the spinal column 42 represents the y-axis in a two-dimensional x-y plot, the CP 18 can plot the x-y coordinates of the locations of the electrodes 26 within the plot, and compute the title angle using simple geometric principles. The retrograde properties of the neurostimulation leads 12 (i.e., whether the distal tips of the neurostimulation leads 12 face in the rostral direction or the caudal direction) may be determined by the CP 18 based on a known insertion point of the neurostimulation leads 12 into the spinal column 42, which insertion point can either be manually input into the CP 18 by the user or determined based on a series of fluoroscopic images or static X-ray images of the neurostimulation leads 12 as they are advanced along the spinal column 42 during implantation into the patient 40.

Figure 6:
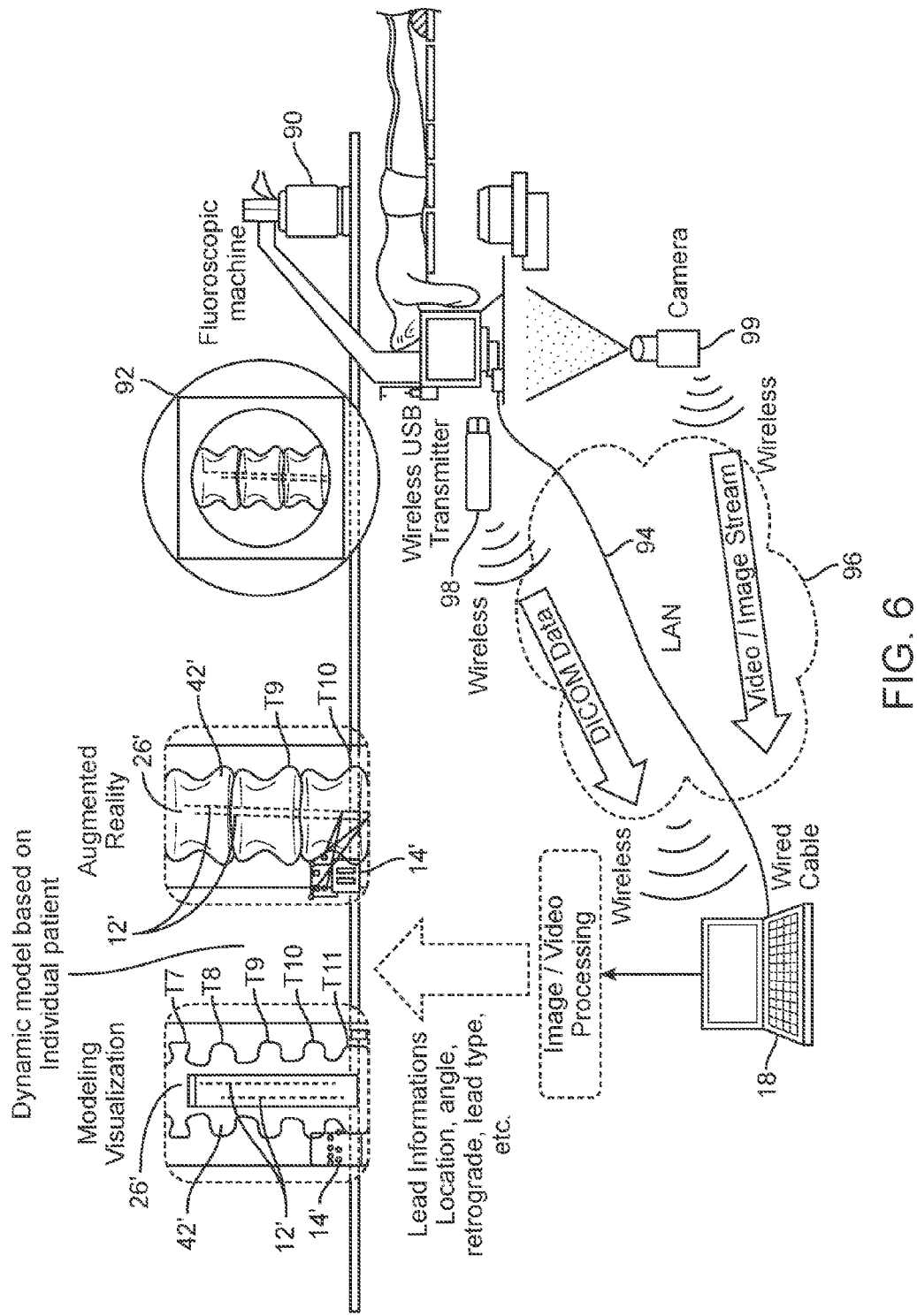
FIG. 6 is a plan view of system in which the clinician programmer (CP) of FIG. 5 can be incorporated for acquiring and detecting the locations of neurostimulation leads in a medical image.

Once the locations, tilt angle, and retrograde property of the neurostimulation leads 12 are determined, the CP 18 may generate/reconstruct a representation of the neurostimulation leads 12' and display it in the context of a representation of the spinal column 42' on the display screen 76, as illustrated in FIG. 6. The CP 18 may display virtual objects, such as a graphical representation of the IPG 14', along with its ports (not shown) and coupling links to the neurostimulation leads 12, thereby allowing the user to interact with these objects in the context of the representations of the neurostimulation leads 12' and spinal column 42'. Further details discussing the graphical coupling of the ports of an IPG 14 to selected neurostimulation leads 12 are described in U.S. Provisional Patent Application Ser. No. 61/694,695, entitled "System and Method for Connecting Devices to a Neurostimulator," which is expressly incorporated herein by reference.

In one embodiment, the representation of the neurostimulation leads 12' takes the form of a graphical lead model represented by graphical representations of electrodes 26' spaced apart in accordance with predetermined electrode spacings. This graphical lead model may be stored in the memory 66, and if different types of neurostimulation leads 12 are contemplated, multiple graphical lead models may be stored in a look-up table with corresponding lead types. The CP 18 will thus select the graphical lead model corresponding to the type of the neurostimulation leads 12. As previously discussed, the type of the neurostimulation leads 12 may either be manually input into the CP 18 or can be automatically detected by the CP 18 by recognizing patterns of the electrodes 26 in the medical image data. Alternatively, independent graphical representations of the electrodes 26' (in a suitable geometric shape, such as a rectangle) may simply be respectively located at the identified locations of the electrodes 26.

In this embodiment, the graphical representation of the spinal column 42' takes the form of a graphical model, which may be homogenous or may be patient-specific in that the spinal column model 42' may be scaled in accordance with the size of the spinal column 42 identified by the CP 18 in the medical image data. That is, if the CP 18 determines that the spinal column 42 of the patient 40 is relatively large, the CP 18 may scale the size of the spinal column representation 42' up, and if the CP 18 determines that the spinal column 42 of the patient 40 is relatively small, the CP 18 may scale the size of the spinal column representation 42' down or even the scale of each segment size accordingly. The significance is that the ratio between the size of the neurostimulation leads 12 and the spinal column 42 of the patient 40 should match the ratio between the size of the graphical representation of the neurostimulation leads 12' and the spinal column representation 42' displayed on the CP 18. In any event, the CP 18 preferably maps the identified locations of the electrodes 26 and spinal column 42 into the graphical coordinate system in which the graphical electrode representations 26' and graphical spinal column representation 42' is rendered.

In another embodiment, the CP 18 displays the medical image, itself, which already contains the representations of the neurostimulation leads 12' and the representation of the spinal column 42'. The medical image may be displayed as an augmented reality image in that virtual components, such as a graphical representation of the IPG 14', along with its ports and coupling links to the neurostimulation leads 12, can be displayed on the medical image, thereby allowing the user to interact with these objects in the context of the representations of the neurostimulation leads 12' and spinal column 42'.

In an optional embodiment, after the CP 18 has automatically determined the locations of the neurostimulation leads 12 relative to the spinal column 42 and relative to each other, the CP 18 allows the user to manipulate the locations of graphical representations of the neurostimulation leads 12' relative to the representation of the spinal column 42'; for example, by dragging the leads 12 using a pointing device in the manner described in U.S. patent application Ser. No. 13/104,826, entitled "System and Method for Defining Neurostimulation Lead Configurations," which is expressly incorporated herein by reference. This feature is useful when the user believes that the locations of the neurostimulation leads 12 automatically determined by the CP 18 need to be adjusted or otherwise refined.

The CP 18 also optionally allows the user to assist the automated lead location process in certain cases. For example, if the medical image data received by the CP 18 is of poor quality, such that the CP 18 is not able to ascertain the vertebral segments of the spinal column 42 in the medical image, the CP 18 may display the medical image on the display screen 76, and allow the user to graphically mark the relevant vertebral segments directly on the displayed medical image using a pointing device; for example, by marking T7 of the vertebral segment believed to correspond with T7 on the medical image. The CP 18, with knowledge of the graphically marked vertebral segment or segments, can then more accurately detect the location of the neurostimulation leads 12 relative to the spinal column 72.

Once the location of the neurostimulation leads 12 relative to the spinal column 42 and to each other, the tilt angle of the neurostimulation leads 12 relative to the midline of the spinal column 42, retrograde properties of the neurostimulation leads 12, and type of neurostimulation leads 12, are determined, the CP 18, in response to user input, generates a set of stimulation parameters based on this lead information. In particular, the CP 18 provides a user interface that conveniently allows a user to program the IPG 14. In this illustrated embodiment, the CP 18 displays the graphical lead representations 12' properly located in the context of the spinal column representation 42' to provide a convenient reference for the user when programming the IPG 14, as well as inputs the lead location information into the algorithm or algorithms used by the CP 18 during current steering. The particular current steering technique may be performed by the CP 18 using, e.g., virtual target poles to steer the current within the electrode array, as described in U.S. Provisional Patent Application Ser. No. 61/452,965, entitled "Neurostimulation System for Defining a Generalized Virtual Multipole," which is expressly incorporated herein by reference. Alternatively, the particular current steering technique performed by the CP 18 may use predefined steering tables to steer the current within the electrode array, as described in U.S. patent application Ser. No. 12/614,942, entitled "System and Method for Determining Appropriate Steering Tables for Distributing Stimulation Energy Among Multiple Neurostimulation Electrodes," which is also expressly incorporated herein by reference.

Significantly, as briefly discussed above, the thickness of the cerebral spinal fluid (CSF) varies along the length of the spinal cord, and thus, the neurostimulation leads 12 may be subjected to a different volume of CSF depending on their location relative to the longitudinal vertebral segments. However, with knowledge of the locations of the neurostimulation leads 12 relative to the longitudinal vertebral segments, the CP 18 can select or adjust a current steering algorithm that is more appropriate for the assumed CSF thickness. For example, if the CSF thickness is relatively large, the CP 18 may select a current steering algorithm that results in relatively large spacings between the active anode(s) and cathode(s) to reduce the shunting of current between the electrodes, thereby reducing the stimulation threshold of the relevant spinal cord tissue. In contrast, if the CSF thickness is relatively small, the CP 18 may select a current steering algorithm that results in relatively small spacings between the active anode(s) and cathode(s) to enhance the tunability of the electrodes. To aid in this function, a look-up table containing the vertebral segment locations and corresponding CSF thicknesses along with the specific current steering algorithms (e.g., in the form of different virtual pole configurations or different pre-defined steering tables) may be stored in the memory 66.

Figure 7:
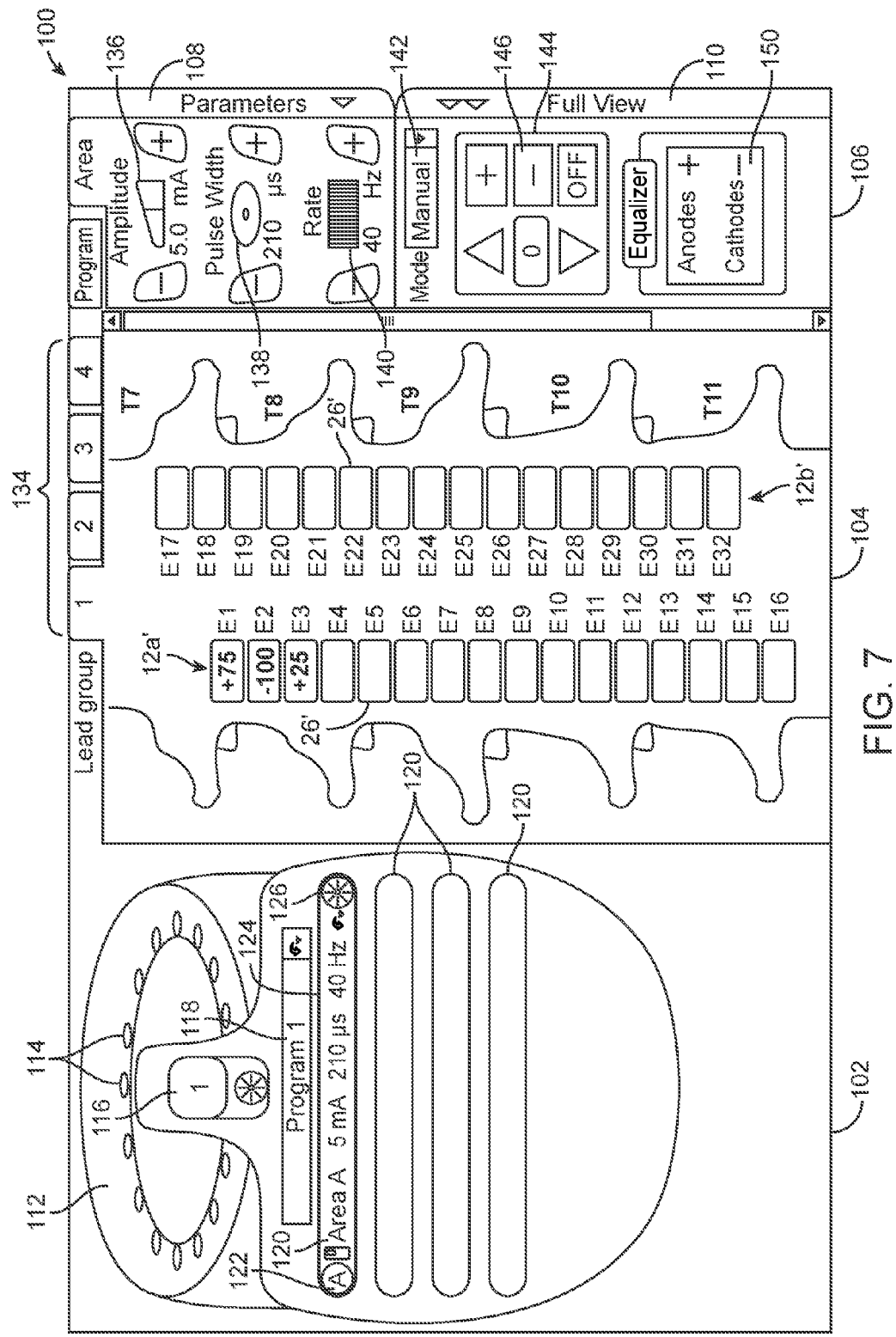
FIG. 7 is a plan view of a user interface of the CP of FIG. 5 for programming the IPG of FIG. 3 in a manual programming mode.

Referring first to FIG. 7, a graphical user interface (GUI) 100 that can be generated by the CP 18 to allow a user to program the IPG 14 will be described. In the illustrated embodiment, the GUI 100 comprises three panels: a program selection panel 102, a lead display panel 104, and a stimulation parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about stimulation programs and coverage areas that have been, or may be, defined for the IPG 14. In particular, the program selection panel 102 includes a carousel 112 on which a plurality of stimulation programs 114 (in this case, up to sixteen) may be displayed and selected. The program selection panel 102 further includes a selected program status field 116 indicating the number of the stimulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected stimulation program 114. In the illustrated embodiment, currently selected program 1 has been called "lower back," thereby identifying program 1 as being the stimulation program 114 designed to provide therapy for lower back pain.

The program selection panel 102 further comprises a plurality of coverage areas 120 (in this case, up to four) with which a plurality of stimulation parameter sets can respectively be associated to create the currently selected stimulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the stimulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the stimulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective stimulation parameter sets associated with the coverage areas 120. Thus, each coverage area 120 corresponds to a timing channel. Once selected, the coverage area 120 will be populated with the designation field 122, electrical pulse parameter field 124, and selection icon 126.

The lead display panel 104 includes the neurostimulation lead representations 12' in the context of the spinal column representation 42'. Each of the lead representations 12' includes sixteen electrode representations 26' (labeled electrodes E1-E16 for the first lead representation 12(a)' and electrodes E17-E32 for second lead representation 12(b)'. Although the programming screen 100 displays representations of the two percutaneous leads 12 illustrated in FIG. 3, it should be appreciated that the programming screen 100 can display a representation of any neurostimulation lead including the surgical paddle neurostimulation lead illustrated in FIG. 4. The lead display panel 104 further includes lead group selection tabs 134 (in this case, four), any of which can be actuated to select one of four groups of leads 12. In this case, the first lead group selection tab 134 has been actuated, thereby displaying the two leads 12 in their defined orientation. In the case where additional leads 12 are implanted within the patient, they can be associated with additional lead groups.

The parameters adjustment panel 106 also includes a pulse amplitude adjustment control 136 (expressed in milliamperes (mA)), a pulse width adjustment control 138 (expressed in microseconds (μs)), and a pulse rate adjustment control 140 (expressed in Hertz (Hz)), which are displayed and actuatable in all the programming modes. Each of the controls 136-140 includes a first arrow that can be actuated to decrease the value of the respective stimulation parameter and a second arrow that can be actuated to increase the value of the respective stimulation parameter. Each of the controls 136-140 also includes a display area for displaying the currently selected parameter. In response to the adjustment of any of electrical pulse parameters via manipulation of the graphical controls in the parameter adjustment panel 106, the controller/processor 80 generates a corresponding stimulation parameter set (with a new pulse amplitude, new pulse width, or new pulse rate) and transmits it to the IPG 14 via the telemetry circuitry 86 for use in delivering the modulation energy to the electrodes 26.

The parameter adjustment panel 106 includes a pull-down programming mode field 142 that allows the user to switch between a manual programming mode, an electronic trolling programming mode, and a navigation programming mode. Each of these programming modes allows a user to define a stimulation parameter set for the currently selected coverage area 120 of the currently selected program 114 via manipulation of graphical controls in the parameter adjustment panel 106 described above, as well as the various graphical controls described below. In the illustrated embodiment, when switching between programming modes via actuation of the programming mode field 142, the last electrode configuration with which the IPG 14 was programmed in the previous programming mode is converted into another electrode configuration, which is used as the first electrode configuration with which the IPG 14 is programmed in the subsequent programming mode. The electronic trolling programming mode is designed to quickly sweep the electrode array using a limited number of electrode configurations to gradually steer an electrical field relative to the modulation leads until the targeted modulation site is located. Using the electrode configuration determined during the electronic trolling programming mode as a starting point, the navigation programming mode is designed to use a wide number of electrode configurations to shape the electrical field, thereby fine tuning and optimization the modulation coverage for patient comfort.

As shown in FIG. 7, the manual programming mode has been selected. In the manual programming mode, each of the electrodes 26' of the lead representations 12' may be individually selected, allowing the clinician to set the polarity (cathode or anode) and the magnitude of the current (percentage) allocated to that electrode 26 using graphical controls located in an amplitude/polarity area 144 of the parameter adjustment panel 106.

In particular, a graphical polarity control 146 located in the amplitude/polarity area 144 includes a "+" icon, a "−" icon, and an "OFF" icon, which can be respectively actuated to toggle the selected electrode 26 between a positive polarization (anode), a negative polarization (cathode), and an off-state. An amplitude control 148 in the amplitude/polarity area 144 includes an arrow that can be actuated to decrease the magnitude of the fractionalized current of the selected electrode 26, and an arrow that can be actuated to increase the magnitude of the fractionalized current of the selected electrode 26. The amplitude control 148 also includes a display area that indicates the adjusted magnitude of the fractionalized current for the selected electrode 26. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 80 generates a corresponding stimulation parameter set (with a new fractionalized electrode combination) and transmits it to the IPG 14 via the telemetry circuitry 86 for use in delivering the modulation energy to the electrodes 26.

In the illustrated embodiment, electrode E2 has been selected as a cathode to which 100% of the cathodic current has been allocated, and electrodes E1 and E3 have been respectively selected as anodes to which 25% and 75% of the anodic current has been respectively allocated. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference. The parameters adjustment panel 106, when the manual programming mode is selected, also includes an equalization control 150 that can be actuated to automatically equalize current allocation to all electrodes of a polarity selected by respective "Anode +" and "Cathode −" icons.

Figure 8:
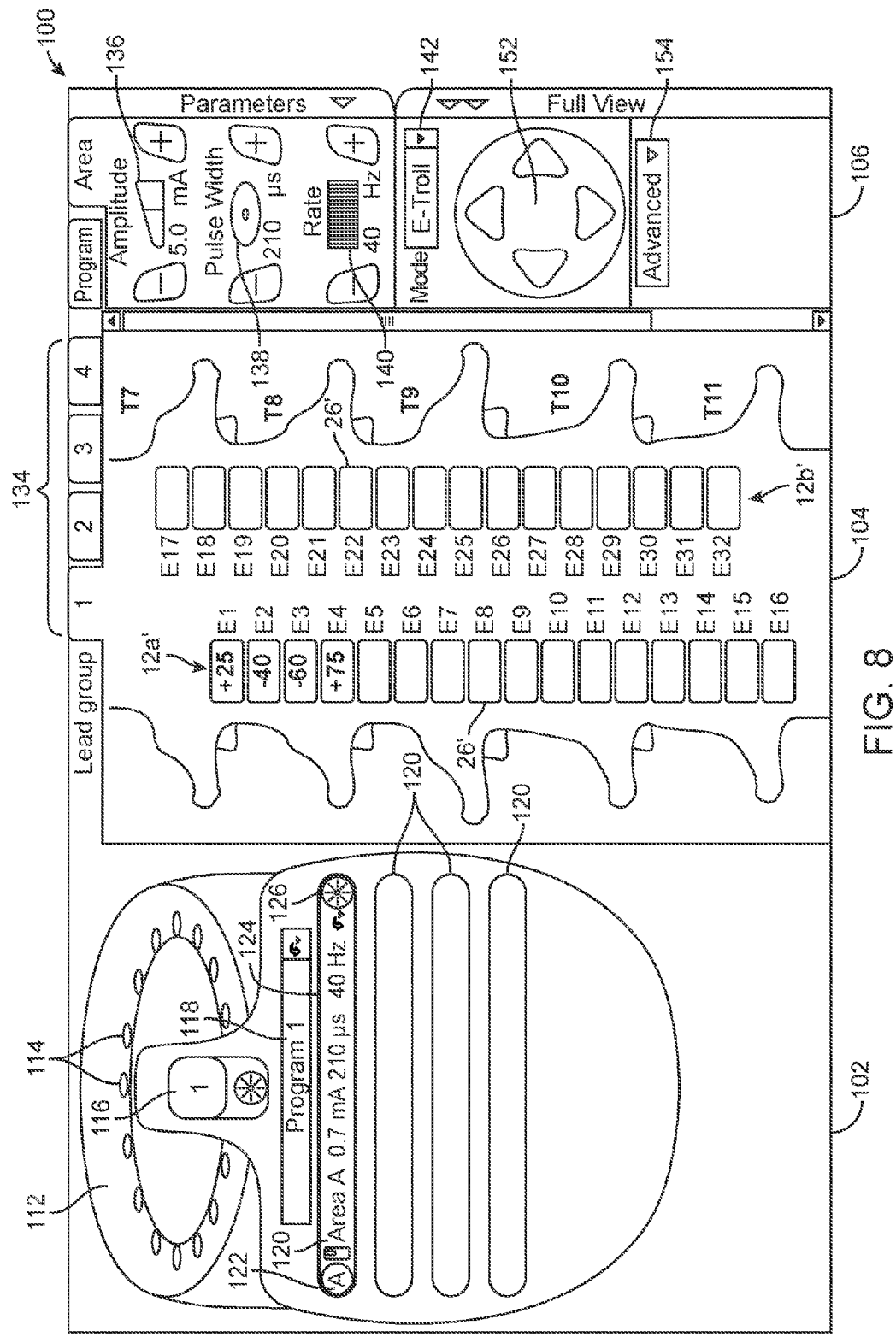
FIG. 8 is a plan view of a user interface of the CP of FIG. 5 for programming the IPG of FIG. 3 in an electronic trolling programming mode.

As shown in FIG. 8, the electronic trolling programming mode has been selected. In this mode, the electrode representations 26' illustrated in the lead display panel 104 that were individually selectable and configurable in manual programming mode are used for display only and are not directly selectable or controllable. Instead of an amplitude/polarity area 144, the parameter selection panel 106 includes a steering array of arrows 152 that allows steering the electrical field up, down, left, or right relative to the electrodes 26. In the illustrated embodiment, fractionalized cathodic currents of 40% and 60% have been respectively computed for electrodes E2 and E3, and fractionalized anodic currents of 25% and 75% have been computed for electrodes E1 and E4. In response to the steering of the electrical current via manipulation of the steering array of arrows 152, the controller/processor 80 generates a series of stimulation parameter sets (with different fractionalized electrode combination) and transmits them to the IPG 14 via the telemetry circuitry 86 for use in delivering the stimulation energy to the electrode array 26 in a manner that steers the locus of the resulting electrical field relative to the electrode array 26.

Figure 9:
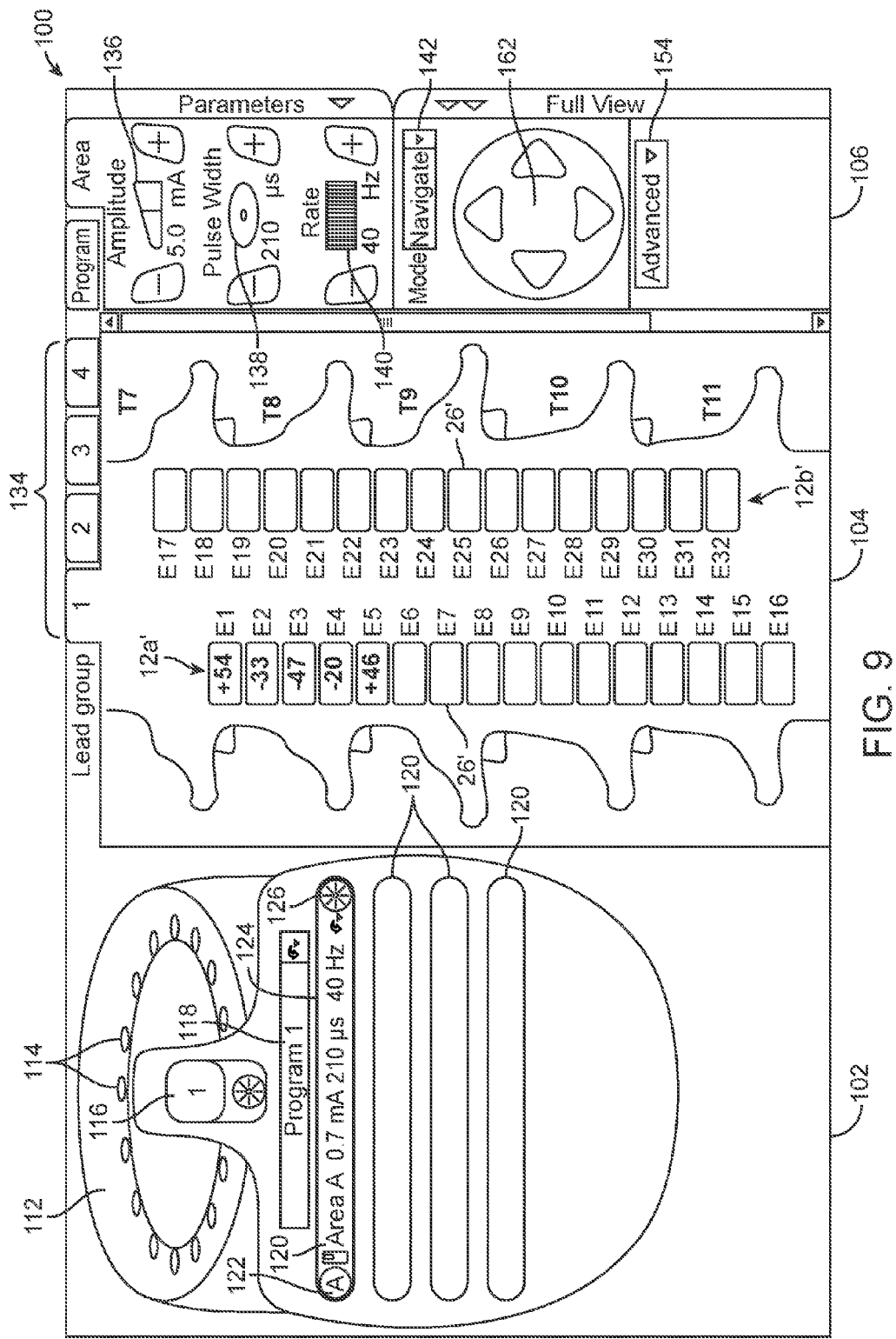
FIG. 9 is a plan view of a user interface of the CP of FIG. 5 for programming the IPG of FIG. 3 in a navigation programming mode.

As shown in FIG. 9, the navigation programming mode has been selected. As in the electronic trolling programming mode, the electrodes illustrated in the lead display panel 104 that were individually selectable and configurable in manual programming mode are used for display only and are not directly selectable or controllable in the navigation programming mode, and instead of an amplitude/polarity area 144, the The parameter selection panel 106 includes a steering array of arrows 162 that allows steering the electrical field up, down, left, or right relative to the electrodes 26. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole. In the illustrated embodiment, fractionalized cathodic currents of 33%, 47%, and 20% have been respectively computed for electrodes E2, E3, and E4, and fractionalized anodic currents of 54% and 46% have been respectively computed for electrodes E1 and E5. In response to the steering of the electrical current via manipulation of the steering array of arrows 162, the controller/processor 80 generates a series of stimulation parameter sets (with different fractionalized electrode combinations) and transmits them to the IPG 14 via the telemetry circuitry 86 for use in delivering the modulation energy to the electrode array 26 in a manner that steers the locus of the resulting electrical field relative to the electrode array 26.

It can be appreciated from the foregoing that the ability of the CP 18 to automatically detect lead information and spinal column information in the medical image data may provide a more accurate model of the spinal column when displayed to the user, provides more precise lead position information than does manual entry of the lead position information, and integrates both lead detection and lead programming in a single real-time system that can be used during surgery, as well as off-line during subsequent programming in a post-op setting.

Although the foregoing technique has been described as being implemented in the CP 18, it should be noted that this technique may be alternatively or additionally implemented in the RC 16. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system, comprising:
   a user interface configured to receive a user input;
   control/processing circuitry configured to:
     process a medical image of at least one neurostimulation lead relative to an anatomical structure to detect a location of the at least one neurostimulation lead relative to the anatomical structure; and
     use both the user input and the detected location to generate a set of stimulation parameters that control electrical energy delivered from the at least one neurostimulation lead.

2. The system of claim 1, wherein the medical image is a fluoroscopic image.

3. The system of claim 1, wherein the medical image is a static X-ray image.

4. The system of claim 1, further comprising communication circuitry configured to receive the medical image from a machine that created the medical image.

5. The system of claim 4, wherein the communication circuitry is configured to communicate with the machine that created the medical image using a wired connection to the machine, and to receive the medical image using the wired connection to the machine.

6. The system of claim 4, wherein the communication circuitry is configured to wirelessly communicate with the machine that created the medical image, and to receive the medical image using the wired connection to the machine.

7. The system of claim 1, wherein the set of stimulation parameters include electrode combinations that define electrodes on the lead that are activated, and that further define the activated electrode(s) that function as an anode and the activated electrode(s) that function as a cathode.

8. The system of claim 7, wherein the set of stimulation parameters includes fractional electrode combinations that define a percentage of stimulation energy assigned to each electrode.

9. The system of claim 1, wherein the anatomical structure includes a spinal column.

10. The system of claim 9, wherein the control/processing circuitry is configured to process the medical image to detect a location of the at least one neurostimulation lead relative to vertebral segments.

11. The system of claim 10, wherein the control/processing circuitry is configured to linearly interpolate between vertebral segments to determine the location of the at least one neurostimulation lead.

12. The system of claim 1, wherein the control/processing circuitry is configured use a reference point on the at least one neurostimulation lead to detect the location of the at least one neurostimulation lead relative to vertebral segments.

13. The system of claim 1, wherein the control/processing circuitry is further configured identify locations of two or more neurostimulation leads relative to each other, or identify a tilt angle of the at least one neural stimulation lead relative to a midline of a spinal column.

14. The system of claim 1, wherein the control/processing circuitry and the user interface are configured to cooperate to display a graphical representation of the at least one neurostimulation lead relative to a representation of the anatomical structure.

15. The system of claim 1, wherein the control/processing circuitry is configured for processing the medical image using an image segmentation and pattern recognition technique.

16. A method of operating an external system having a user interface and control/processing circuitry, the method comprising:
receiving a user input using the user interface;
using the control/processing circuitry to access a medical image of at least one neurostimulation lead relative to an anatomical structure, detect a location of the at least one neurostimulation lead relative to the anatomical structure, and generate a set of stimulation parameters using both the received user input and the detected location, the set of stimulation parameters to control electrical energy delivered from the at least one neurostimulation lead.

17. The method of claim 16, further comprising using the user interface to prompt a user to provide the user input.

18. The method of claim 16, further comprising communicating the set of stimulation parameters from the external system to an implanted neurostimulator for use by the implanted neurostimulator to control electrical energy delivered from the at least one neurostimulation lead.

19. The method of claim 16, wherein using the control/processing circuitry to detect the location includes processing the medical image using an image segmentation and pattern recognition technique.

20. The method of claim 16, further comprising display a graphical representation of the at least one neurostimulation lead relative to a representation of the anatomical structure.

* * * * *